United States Patent [19]

Henrick

[11] Patent Number: 4,647,698

[45] Date of Patent: Mar. 3, 1987

[54] NOVEL COMPOSITIONS

[75] Inventor: Clive A. Henrick, Palo Alto, Calif.

[73] Assignee: Sandoz Ltd., Palo Alto, Calif.

[21] Appl. No.: 649,875

[22] Filed: Sep. 13, 1984

[51] Int. Cl.$^4$ .................. C07C 131/00; C07C 93/00
[52] U.S. Cl. ............................ 564/256; 564/300;
546/264; 546/283; 546/284; 546/300; 546/334;
549/59; 549/60; 549/65; 549/75; 549/472;
549/473; 549/479; 549/491; 549/494; 549/495
[58] Field of Search .................. 564/256, 265, 300;
546/264, 283, 284, 300, 334; 549/59, 60, 65, 75,
472, 473, 479, 491, 494, 495

[56] References Cited

U.S. PATENT DOCUMENTS 3,137,705  6/1964  Prelog et al. ................. 564/300
3,184,510  5/1965  Levy ............................. 564/256

FOREIGN PATENT DOCUMENTS 1517774  2/1968  France ........................ 564/256
2115812  9/1983  United Kingdom .

OTHER PUBLICATIONS

Kumar, Yatendra et al., *Acta Pharm. Suec.*, vol. 20, (1983), pp. 349–364.
Conant, James Bryant et al., *The Chemistry of Organic Compounds*, 4th Ed. (1955), MacMillan, publ. p. 335.

*Primary Examiner*—Natalie Trousof
*Assistant Examiner*—L. Hendriksen
*Attorney, Agent, or Firm*—Hana Dolezalova; Jacqueline S. Larson

[57] ABSTRACT

Substituted oximes and hydroxylamine ethers, intermediates therefor, synthesis thereof, and their use for the control of pests.

22 Claims, No Drawings

NOVEL COMPOSITIONS

This invention relates to novel substituted oximes and hydroxylamine ethers, intermediates therefor, synthesis thereof, and the use of the compounds for the control of pests.

More particularly, the compounds of the present invention are represented by the following formulas (A) and (B):

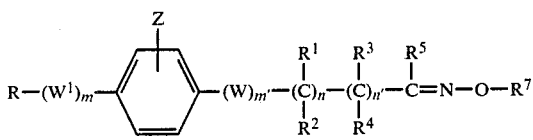

(A)

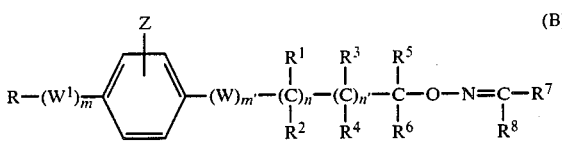

(B)

wherein,
each of m and m' is independently zero or one;
each of n and n' is independently zero, one, two or three;
R is hydrogen, lower alkyl, lower alkenyl, lower alkynyl, lower haloalkyl, lower haloalkenyl, lower haloalkynyl, lower alkoxyalkyl, lower alkylthioalkyl, cycloalkyl, halocycloalkyl, cycloalkylalkyl, heterocycloalkyl, or heterocycloalkylalkyl;
each of $R^1$, $R^2$, $R^3$, $R^4$, $R^5$, $R^6$ and $R^9$ is independently hydrogen or lower alkyl, provided that: 1) when n is one and n' is zero, then $R^1$ and $R^5$ can together form an alkylene bridge of two to four carbon atoms, or 2) when each of n and n' is one, then either $R^1$ and $R^3$ or $R^3$ and $R^5$ or $R^1$ and $R^5$ can together form an alkylene bridge of two to four carbon atoms;
each of $R^7$ and $R^8$ is independently hydrogen, lower alkyl, lower haloalkyl, lower alkenyl, lower alkynyl, lower alkoxy, lower alkylthio, lower alkoxyalkyl, lower alkylthioalkyl, substituted or unsubstituted phenyl, pyridyl, furyl or thienyl; or $R^7$ and $R^8$ together form a saturated or unsaturated 5- or 6-membered ring containing from zero to two oxygen or sulfur atoms;
W is oxygen, sulfur, $NR^9$ or carbonyl;
$W^1$ is oxygen, sulfur, sulfinyl, sulfonyl, $NR^9$ or carbonyl; and
Z is hydrogen, lower alkyl, lower haloalkyl or halogen.

In the description hereinafter and the appended claims, each of m, m', n, n', $R$-$R^9$, W, $W^1$ and Z is as defined above, unless otherwise specified.

The compounds of the present invention of formula (A) can be prepared by reacting a ketone of formula (I) with a substituted hydroxylamine of formula (II) in a solvent such as dioxane and in the presence of pyridine, at room temperature or above.

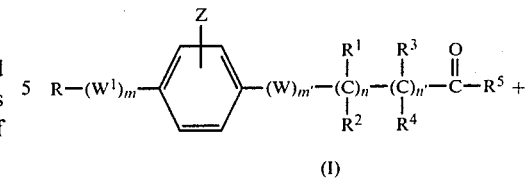

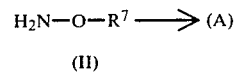

Compounds of formula (B) can be prepared by the reaction of an oxime (IV) with sodium hydride and then with a halide or methanesulfonate (III; Q is halo atom or mesyl group), in an organic solvent such as N-methylpyrrolidone, dimethylformamide or tetrahydrofuran and at room temperature or below.

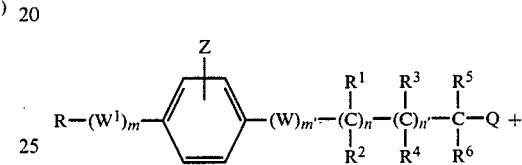

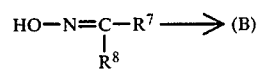

Compounds of formula A or B where $W^1$ is sulfinyl are prepared by reacting a compound of formula A or B where $W^1$ is sulfur with one equivalent of sodium periodate or m-chloroperbenzoic acid in a solvent such as methanol or methylene chloride. Compounds where $W^1$ is sulfonyl are prepared in the same manner, except that two equivalents of m-chloroperbenzoic acid are used. Alternatively, either hydrogen peroxide in warm acetic acid or excess hydrogen peroxide with selenium dioxide is used as the oxidant.

The starting materials of formulas I through IV are known compounds, or they can be produced by methods analogous to known methods described in the literature, such as, for example, methods disclosed in U.K. GB 2,115,812 and European EP 89,115. For example, the compound of formula (I) can be prepared by reacting a phenol, thiophenol or aniline (V) with a halide or methanesulfonate (VI; Q is a halo atom or mesyloxy) in the presence of a base.

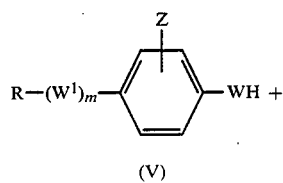

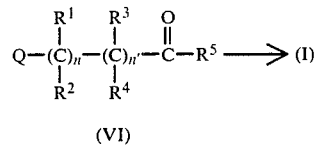

The compound (III) can be prepared by reacting a ketone (I) with lithiumaluminumhydride to make the corresponding alcohol (VII), which is then halogenated, for example, to (III).

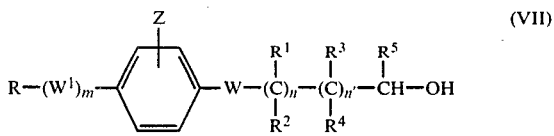
(VII)

Alternatively, the compound (III) can be prepared by reacting a phenol, thiophenol or aniline (V) with a halide or methanesulfonate (VIII; Q is a halo atom or mesyloxy) in the presence of a base.

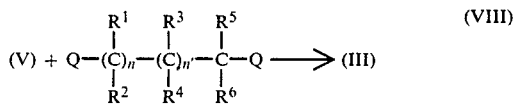
(VIII)

The compounds of the present invention of formulas A and B can have one or more asymmetric centers and/or geometric isomers. The present invention includes each of the stereo isomers and the mixtures of stereo isomers thereof. In the examples hereinafter, unless otherwise specified, the compound is a mixture of stereo isomers.

Also included within the scope of the present invention are substituted hydroxylamine ethers of the following formulas C and D:

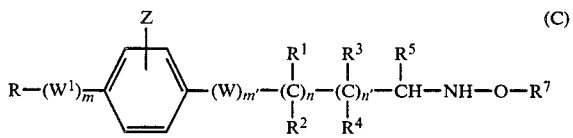
(C)

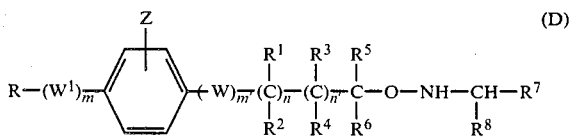
(D)

wherein the values for m, m', n, n', R-R$^8$, W, W$^1$ and Z are as defined above.

The above hydroxylamine ethers are prepared by reducing the corresponding oximes with sodium cyanoborohydride, as described in Tetrahedron Letters 29:2493-2496 (1974), or with pyridineborane in acid media, such as ethanol-10% aqueous HCl or 20% ethanolic hydrogen chloride, as described in *Ventron Alembic*, Issue #29 (1983).

The compounds of the present invention of formulas A-D are useful pest control agents, particularly for the control of insects, mites and ticks. The utility of these compounds as pest control agents is believed to be attributable to their juvenile hormone activity. They are preferably applied to the immature pest, namely during the embryo, larval or prepupal stage, in view of their effect on metamorphosis and otherwise abnormal development leading to death or inability to reproduce. These compounds can be effective control agents for insects of, for example, the orders Lepidoptera, Hemiptera, Homoptera, Coleoptera, Diptera, Orthoptera, and Siphonaptera, and other insects, and mites and ticks of the class Acari, including mites of the families Tetranychidae and Tarsonemidae and ticks of the families Argasidae and Ixodidae. The compounds can be applied to the pest or its locus in a pest controlling amount, usually of the order of 0.1 μg to 100 μg per insect, mite or tick.

In the use of the compounds of formulas A-D for combatting insects, a compound of formula A, B, C or D or mixtures thereof, can be combined with a carrier substance for application to the locus. The carrier can be liquid or solid and include adjuvants such as wetting agents, dispersing agents and other surface active agents. The compounds can be used in formulations such as wettable powders, solutions, dusts, granules, emulsifiable concentrates and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A, B, C or D in the formulation can vary widely, generally within the range of about 0.01 percent to 90.0 percent, by weight. Generally, a concentration of less than 25 percent of the active compound is employed.

The compounds of formulas A-D can be combined with a cyclodextrin to make a cyclodextrin inclusion complex for application to the pest or its locus.

The compounds of the present invention can be used in combination with other pesticides such as the synthetic pyrethroids, carbamates, phosphates and insect growth regulators, or with insect attractants.

The following terms, wherever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to six halogen atoms.

The term "lower alkenyl" refers to an alkenyl group, straight or branched, having a chain length of two to eight carbon atoms and one or two ethylenic bonds. The term "lower haloalkenyl" refers to a lower alkenyl group substituted with one to six halogen atoms.

The term "lower alkynyl" refers to an alkynyl group, straight or branched, having a chain length of two to eight carbon atoms and one or two acetylenic bonds. The term "lower haloalkynyl" refers to a lower alkynyl group substituted with one to six halogen atoms.

The term "lower alkoxyalkyl" refers to an alkyl group substituted at one of the carbon atoms by an alkoxy group, straight or branched, the total number of carbon atoms being not greater than ten.

The term "lower alkylthioalkyl" refers to a lower alkyl group substituted at one of the carbon atoms by an alkylthio group, straight or branched, the total number of carbon atoms being not greater than ten.

The term "cycloalkyl" refers to a cycloalkyl group of three to eight cyclic carbon atoms. The term "cycloalkylalkyl" refers to a cycloalkyl group wherein one hydrogen atom is replaced by a lower alkyl group, the total number of carbon atoms being from four to twelve. The term "halocycloalkyl" refers to a cycloalkyl group substituted with one to six halogen atoms.

The term "heterocycloalkyl" refers to a heterocycloalkyl group, saturated or unsaturated, of two to six carbon atoms and one to three atoms selected from nitrogen, oxygen or sulfur. The term "heterocycloalkylalkyl" refers to a heterocycloalkyl group wherein one hydrogen is replaced by a lower alkyl group, the total number of carbon atoms being from three to twelve.

The term "substituted phenyl" refers to a phenyl group substituted at one, two or three of the ring carbon atoms with a group selected from lower alkyl, lower haloalkyl, lower alkoxy, lower haloalkoxy, halogen, nitro, cyano and lower alkylthio.

The following examples are provided to illustrate the practice of the present invention. Temperature is given in degrees Centigrade. RT stands for room temperature.

EXAMPLE 1

To a mixture of 4-(1-methylpropoxy)phenoxyacetaldehyde (0.68 g, 3.3 mmol) and pyridine (0.50 g, 6.3 mmol) in 5 ml of p-dioxane is added a solution of ethoxyamine hydrochloride (0.60 g, 6.2 mmol) in a minimum amount of water. The reaction mixture is stirred at RT for 6 hours, after which the dioxane is removed in vacuo. The residue is taken up in ether and the organic layer is washed with water. The aqueous phase is extracted with ether, and the combined organic phases are dried, the solvent is removed in vacuo and the product is purified by column chromatography to give 4-(1-methylpropoxy)phenoxyacetaldehyde O-ethyloxime as a mixture of syn and anti stereo isomers. MS m/e 251 (M+).

nmr (CDCl$_3$) δ 1.0–2.0 (m, 11 H, CH$_3$-CH$_2$-CH(CH$_3$)-O, O-CH$_2$-CH$_3$), 3.8–4.5 (m, 5 H, CH(CH$_3$)-O, O-CH$_2$-CH=N, O-CH$_2$-CH$_3$), 6.8 (s, 4 H, aromatic) and 8.3 ppm (m, 1 H, CH=N).

EXAMPLE 2

To a mixture of 4-(1-methylpropoxy)phenoxyacetone (0.70 g, 3.1 mmol) and pyridine (0.50 g, 6.3 mmol) in 10 ml of p-dioxane is added a solution of ethoxyamine hydrochloride (0.70 g, 7.2 mmol) in a minimum amount of water. The reaction mixture is stirred at RT for 16 hours, after which the dioxane is removed in vacuo. The residue is taken up in ether and the organic layer is washed with water. The aqueous phase is extracted with ether, and the combined organic phases are dried, the solvent is evaporated off and the product is purified by column chromatography to give 4-(1-methylpropoxy)phenoxyacetone O-ethyloxime, MS m/e 265 (M+).

nmr (CDCl$_3$) δ 0.8–1.8 (m, 11 H, CH$_3$-CH$_2$-CH(CH$_3$)-O, O-CH$_2$-CH$_3$), 2.0 (s, 3H, C(CH$_3$)=N), 3.9–4.8 (m, 5 H, CH(CH$_3$)-O, O-CH$_2$-C(CH$_3$)=N, O-CH$_2$-CH$_3$) and 6.8 ppm (s, 4 H, aromatic).

EXAMPLE 3

Following the procedure of Examples 1 and 2, each of the ketones under column I is reacted with ethoxyamine hydrochloride to give the corresponding O-ethyloxime under column II.

I 1. 4-[4-(1-methylpropoxy)phenoxy]-2-butanone
2. 4-[4-(1-methylpropoxy)phenoxy]-2-pentanone
3. 1-[4-(1-methylpropoxy)phenoxy]-2-butanone
4. 4-(3-methyl-2-butenoxy)phenoxyacetone
5. 4-(1-methylbutoxy)phenoxyacetone
6. 4-(3-methoxy-3-methylbutoxy)phenoxyacetone
7. 4-(3-chloro-2-propenoxy)phenoxyacetone
8. 4-cyclobutoxyphenoxyacetone
9. 4-(1-methylpropylthio)phenoxyacetone
10. 4-(1-methylpropylthio)phenylthioacetone
11. 2-fluoro-4-(1-methylpropoxy)phenoxyacetone
12. 3-chloro-4-(1-methylpropoxy)phenoxyacetone
13. 3-methyl-4-(1-methylpropoxy)phenoxyacetone
14. 5-trifluoromethyl-4-(1-methylpropoxy)phenoxyacetone
15. 2-[4-(1-methylpropoxy)phenoxy]propionaldehyde

II 1. 4-[4-(1-methylpropoxy)phenoxy]-2-butanone O-ethyloxime
2. 4-[4-(1-methylpropoxy)phenoxy]-2-pentanone O-ethyloxime
3. 1-[4-(1-methylpropoxy)phenoxy]-2-butanone O-ethyloxime
4. 4-(3-methyl-2-butenoxy)phenoxyacetone O-ethyloxime
5. 4-(1-methylbutoxy)phenoxyacetone O-ethyloxime
6. 4-(3-methoxy-3-methylbutoxy)phenoxyacetone O-ethyloxime
7. 4-(3-chloro-2-propenoxy)phenoxyacetone O-ethyloxime
8. 4-cyclobutoxyphenoxyacetone O-ethyloxime
9. 4-(1-methylpropylthio)phenoxyacetone O-ethyloxime
10. 4-(1-methylpropylthio)phenylthioacetone O-ethyloxime
11. 2-fluoro-4-(1-methylpropoxy)phenoxyacetone O-ethyloxime
12. 3-chloro-4-(1-methylpropoxy)phenoxyacetone O-ethyloxime
13. 3-methyl-4-(1-methylpropoxy)phenoxyacetone O-ethyloxime
14. 5-trifluoromethyl-4-(1-methylpropoxy)phenoxyacetone O-ethyloxime
15. 2-[4-(1-methylpropoxy)phenoxy]propionaldehyde O-ethyloxime

EXAMPLE 4

Following the procedure of Examples 1 and 2, 4-(1-methylpropoxy)phenoxyacetone is reacted with each of the substituted hydroxylamines under column III to give the corresponding oxime under column IV.

III 16. allyloxyamine
17. propargyloxyamine
18. 4-chlorophenoxyamine
19. 2-pyridyloxyamine
20. 2,2-difluoroethoxyamine
21. 2-furyloxyamine
22. 2-thienyloxyamine

IV 16. 4-(1-methylpropoxy)phenoxyacetone O-allyloxime
17. 4-(1-methylpropoxy)phenoxyacetone O-propargyloxime
18. 4-(1-methylpropoxy)phenoxyacetone O-(4-chlorophenyl)oxime
19. 4-(1-methylpropoxy)phenoxyacetone O-(2-pyridyl)oxime
20. 4-(1-methylpropoxy)phenoxyacetone O-(2,2-difluoroethyl)oxime
21. 4-(1-methylpropoxy)phenoxyacetone O-(2-furyl)oxime
22. 4-(1-methylpropoxy)phenoxyacetone O-(2-thienyl)oxime

EXAMPLE 5

To a solution of 4-(1-methylpropylthio)phenoxyacetone O-ethyloxime (7.1 mmol) in 10 ml of methanol at 0° is added, dropwise over 5 min., sodium periodate (1.67 g, 7.8 mmol) in 13 ml of water. The mixture is stirred for 3 hours while warming to RT. The reaction is worked up by addition of water and extraction with ether. The combined organic extracts are washed with saturated sodium thiosulfate, with water and with brine, dried and solvent evaporated off to give 4-(1-methylpropylsulfinyl)phenoxyacetone O-ethyloxime.

7.1 Mmol of 4-(1-methylpropylthio)phenoxyacetone O-ethyloxime is reacted with 15.6 mmol of m-chloroperbenzoic acid in chloroform to yield 4-(1-methylpropylsulfonyl)phenoxyacetone O-ethyloxime. Alternatively, either hydrogen peroxide in warm acetic acid or excess hydrogen peroxide and selenium dioxide in methanol is used as the oxidant.

EXAMPLE 6

To pentane-washed sodium hydride (0.055 g, 2.3 mmol) in 5 ml of dimethylformamide (DMF), under $N_2$ and below 5°, is added, dropwise and with stirring, acetone oxime (0.16 g, 2.2 mmol) in 5 ml of DMF. The mixture is warmed to RT and is stirred at RT for 2.5 hours, after which 1-methyl-2-[4(1-methylpropoxy)phenoxy]ethyl methanesulfonate (0.50 g, 1.6 mmol) in 5 ml of DMF is added. The reaction mixture is stirred at RT for 18 hours, after which it is poured into water and extracted with ether. The combined organic extracts are washed with water and with brine and dried, solvent is evaporated off and the product is purified by column chromatography to give acetone O-{1-methyl-2-[4-(1-methylpropoxy)phenoxy]phenoxy]ethyl}oxime, MS m/e 279 (M+).

nmr (CDCl$_3$) δ 0.8–1.7 (m, 11 H, CH$_3$-CH$_2$-CH(CH$_3$)-O, O-CH$_2$-CH(CH$_3$)-O), 1.9 (s, 6 H, N=C(CH$_3$)$_2$), 3.8–4.6 (m, 4 H, CH(CH$_3$)-O, O-CH$_2$-CH(CH$_3$)-O) and 6.8 ppm (s, 4 H, aromatic).

EXAMPLE 7

Following the procedure of Example 6, pentane-washed sodium hydride (0.065 g) is reacted with acetaldehyde oxime (0.15 g). The resulting mixture is reacted with 1-methyl-2-[4-(1-methylpropoxy)phenoxy]ethyl methanesulfonate (0.75 g) to give acetaldehyde O-{1-methyl-2-[4-(1-methylpropoxy)phenoxy]ethyl}oxime.

EXAMPLE 8

Following the procedure of Example 6, 1-methyl-2-[4-(1-methylpropoxy)phenoxy]ethyl methanesulfonate is reacted with each of the oximes under column V to yield the corresponding O-substituted oxime under column VI.

V 1. 3-buten-2-one oxime
2. 3-butyn-2-one oxime
3. 1,4-pentadien-3-one oxime
4. 2-butanone oxime
5. 3-pentanone oxime
6. acetophenone oxime
7. 1-(2-pyridyl)-1-propanone oxime
8. 1-(2-furyl)-1-propanone oxime
9. 1-(2-thienyl)-1-propanone oxime
10. benzophenone oxime
11. cyclohexanone oxime

VI 1. 3-buten-2-one O-{1-methyl-2-[4-(1-methylpropoxy)phenoxy]ethyl}oxime
2. 3-butyn-2-one O-{1-methyl-2-[4-(1-methylpropoxy)phenoxy]ethyl}oxime
3. 1,4-pentadien-3-one O-{1-methyl-2-[4-(1-methylpropoxy)phenoxy]ethyl}oxime
4. 2-butanone O-{1-methyl-2-[4-(1-methylpropoxy)phenoxy]ethyl}oxime
5. 3-pentanone O-{1-methyl-2-[4-(1-methylpropoxy)phenoxy]ethyl}oxime
6. acetophenone O-{1-methyl-2-[4-(1-methylpropoxy)phenoxy]ethyl}oxime
7. 1-(2-pyridyl)-1-propanone O-{1-methyl-2-[4-(1-methylpropoxy)phenoxy]ethyl}oxime
8. 1-(2-furyl)-1-propanone O-{1-methyl-2-[4-(1-methylpropoxy)phenoxy]ethyl}oxime
9. 1-(2-thienyl)-1-propanone O-{1-methyl-2-[4-(1-methylpropoxy)phenoxy]ethyl}oxime
10. benzophenone O-{1-methyl-2-[4-(1-methylpropoxy)phenoxy]ethyl}oxime
11. cyclohexanone O-{1-methyl-2-[4-(1-methylpropoxy)phenoxy]ethyl}oxime

EXAMPLE 9

Following the procedure of Example 6, acetone oxime is reacted with each of the methanesulfonates under column VII to yield the corresponding O-substituted acetone oxime under column VIII.

VII 12. 1-methyl-2-[4-(3-methyl-2-butenoxy)phenoxy]ethyl methanesulfonate
13. 1-methyl-2-[4-(1-methylbutoxy)phenoxy]ethyl methanesulfonate
14. 1-methyl-2-[4-(3-methoxy-3-methylbutoxy)phenoxy]ethyl methanesulfonate
15. 1-methyl-2-[4-(3-chloro-2-propenoxy)phenoxy]ethyl methanesulfonate
16. 1-methyl-2-(4-cyclobutoxyphenoxy)ethyl methanesulfonate
17. 1-methyl-2-[4-(1-methylpropylthio)phenoxy]ethyl methane- sulfonate
18. 1-methyl-2-[4-(1-methylpropylthio)phenylthio]ethyl methanesulfonate
19. 1-methyl-2-[2-fluoro-4-(1-methylpropoxy)phenoxy]ethyl methanesulfonate
20. 1-methyl-2-[3-methyl-4-(1-methylpropoxy)phenoxy]ethyl methanesulfonate
21. 1-methyl-2-[4-(1-methylpropoxy)-5-trifluoromethylphenoxy]ethyl methanesulfonate
22. 1-methyl-3-[4-(1-methylpropoxy)phenoxypropyl methanesulfonate
23. 3-[4-(1-methylpropoxy)phenoxy]butyl methanesulfonate
24. 1-ethyl-2-[4-(1-methylpropoxy)phenoxy]ethyl methanesulfonate
25. 1-methyl-3-[4-(1-methylpropoxy)phenoxy]butyl methanesulfonate
26. 2-[4-(1-methylpropoxy)phenoxy]propyl methanesulfonate
27. 1-methyl-2-[4-methylpropoxy)phenoxy]propyl methanesulfonate
28. 2-[4-(1-methylpropoxy)phenoxy]cyclohexyl methanesulfonate

VIII 12. acetone O-{1-methyl-2-[4-(3-methyl-2-butenoxy)-phenoxy]ethyl}oxime
13. acetone O-{1-methyl-2-[4-(1-methylbutoxy)phenoxy]ethyl}oxime
14. acetone O-{1-methyl-2-[4-(3-methoxy-3-methylbutoxy)phenoxy]ethyl}oxime
15. acetone O-{1-methyl-2-[4-(3-chloro-2-propenoxy)-phenoxy]ethyl}oxime
16. acetone O-[1-methyl-2-(4-cyclobutoxyphenoxyethyl]oxime
17. acetone O-{1-methyl-2-[4-(1-methylpropylthio)-phenoxy]ethyl}oxime
18. acetone O-{1-methyl-2-[4-(1-methylpropylthio)-pyenylthio]ethyl}oxime
19. acetone O-{1-methyl-2-[2-fluoro-4-(1-methylpropoxy)phenoxy]ethyl}oxime
20. acetone O-{1-methyl-2-[3-methyl-4-(1-methylpropoxy)phenoxy]ethyl}oxime
21. acetone O-{1-methyl-2-[4-(1-methylpropoxy)-5-trifluoromethylphenoxy]ethyl}oxime
22. acetone O-{1-methyl-3-[4-(1-methylpropoxy)-phenoxy]propyl}oxime
23. acetone O-{3-[4-(1-methylpropoxy)phenoxy]butyl}oxime
24. acetone O-{1-ethyl-2-[4-(1-methylpropoxy)phenoxy]ethyl}oxime
25. acetone O-{1-methyl-3-[4-(1-methylpropoxy)phenoxy]butyl}oxime
26. acetone O-{2-[4-(1-methylpropoxy)phenoxy]propyl}oxime
27. acetone O-{1-methyl-2-[4-(1-methylpropoxy)phenoxy]propyl}oxime
28. acetone O-{2-[4-(1-methylpropoxy)phenoxy]cyclohexyl}oxime

EXAMPLE 10

Following the procedure of Example 6, propionaldehyde oxime is reacted with each of the methanesulfonates under column IX to yield the corresponding O-substituted propionaldehyde oxime under column X.

IX 29. 2-[4-(1-methylpropoxy)phenoxy]ethyl methanesulfonate
30. 2-[4-(1-methylpropoxy)phenoxy]propyl methanesulfonate
31. 1-methyl-2-[4-(1-methylpropoxy)phenoxy]ethyl methanesulfonate
32. 1-methyl-2-[4-(1-methylpropoxy)phenoxy]propyl methanesulfonate
33. 3-[4-(1-methylpropoxy)phenoxy]butyl methanesulfonate
34. 1-methyl-3-[4-(1-methylpropoxy)phenoxy]propyl methanesulfonate
35. 2-[4-(1-methylpropoxy)phenoxy]cyclohexyl methanesulfonate
36. 2-[4-(3-methyl-2-butenoxy)phenoxy]ethyl methanesulfonate
37. 2-[4-(3-methyl-2-butenoxy)phenoxy]propyl methanesulfonate
38. 2-[4-(1-methylbutoxy)phenoxy]propyl methanesulfonate
39. 2-[4-(3-methoxy-3-methylbutoxy)phenoxy]propyl methanesulfonate
40. 2-[4-cyclobutoxyphenoxy)propyl methanesulfonate
41. 2-[4-(1-methylpropylthio)phenoxy]propyl methanesulfonate
42. 2-[4-(3-methyl-2-butenylthio)phenoxy]propyl methanesulfonate
43. 2-[2-fluoro-4-(1-methylpropoxy)phenoxy]propyl methanesulfonate

X 29. propionaldehyde O-{2-[4-(1-methylpropoxy)-phenoxy]ethyl}oxime
30. propionaldehyde O-{2-[4-(1-methylpropoxy)-phenoxy]propyl}oxime
31. propionaldehyde O-{1-methyl-2-[4-(1-methylpropoxy)phenoxy)ethyl}oxime
32. propionaldehyde O-{1-methyl-2-[4-(1-methylpropoxy)phenoxy]propyl}oxime
33. propionaldehyde O-{3-[4-(1-methylpropoxy)-phenoxybutyl}oxime
34. propionaldehyde O-{1-methyl-3-[4-(1-methylpropoxy)phenoxy]propyl}oxime
35. propionaldehyde O-{2-[4-(1-methylpropoxy)-phenoxy]cyclohexyl}oxime
36. propionaldehyde O-{2-[4-(3-methyl-2-butenoxy)-phenoxy]ethyl}oxime
37. propionaldehyde O-{2-[4-(3-methyl-2-butenoxy) propyl}oxime
38. propionaldehyde O-{2-[4-(1-methylbutoxy)phenoxy]propyl}oxime
39. propionaldehyde O-{2-[4-(3-methoxy-3-methylbutoxy)phenoxy]propyl}oxime
40. propionaldehyde O-[2-(4-cyclobutoxyphenoxy)-propyl]oxime propionaldehyde O-{2-[4-(1-methylpropylthio)phenoxy]propyl}oxime
42. propionaldehyde O-{2-[4-(3-methyl-2-butenylthio) propyl}oxime
43. propionaldehyde O-{2-[2-fluoro-4-(1-methylpropoxy) propyl}oxime

EXAMPLE 11

Following the procedure of Example 6, 3-pentanone oxime is reacted with each of 2-[4-(1-methylpropoxy)-phenoxy]ethyl methanesulfonate, 2-[4-(1-methylpropoxy)phenoxy]propyl methanesulfonate and 2-[4-(3-methyl-2-butenoxy)phenoxy]propyl methanesulfonate to give, respectively, 3-pentanone O-{2-[4-(1-methylpropoxy)phenoxy]ethyl}oxime, 3-pentanone O-{2-[4-(1-methylpropoxy)phenoxy]-propyl}oxime, and 3-pentanone O-{2-[4-(3-methyl-2-butenoxy)phenoxy]-propyl}oxime.

EXAMPLE 12

Following the procedure of Example 1, 4-[4-(1-methylpropoxy)phenyl]-2-butanone (4.41 g, 20.0 mmol) and pyridine (3 ml) in 45 ml of tetrahydrofuran are reacted with ethoxyamine hydrochloride (4.41 g, 45.2 mmol) to give 4-[4-(1methylpropoxy)phenyl]-2-butanone O-ethyloxime, as a mixture of syn and anti stereo isomers. MS m/e 263 (M ).

nmr (CDCl$_3$) δ 1.14–1.63 (t d overlapped, CH(CH$_3$)-O, N-O-CH$_2$-CH$_3$), 1.56 (t, J=7.69, CH$_3$-CH$_2$-CH(CH$_3$)-O), 1.77, 1.83 (s, 3 H, C(CH$_3$)=N), 2.45–2.67 (m, 4 H, CH$_2$-CH$_2$-C(CH$_3$)=N), 3.95–4.26 (m, 3 H, CH(CH$_3$)-O, O-CH$_2$-CH$_3$) and 6.74–7.12 ppm (m, 4 H, aromatic).

EXAMPLE 13

To 4-[4-(1-methylpropoxy)phenyl]-2-butanone O-ethyloxime (2.63 g, 10.0 mmol) in 30 ml of ethanol is added sodium cyanoborohydride (2.00 g, 38.1 mmol) and methanolic 2N HCl is added throughout the reaction to maintain pH at 3. The reaction temperature is maintained at 15°–20°. After ca. 2 hours, the solvent is removed under vacuum. The mixture is made basic by the addition of 10% sodium hydroxide, followed by water and ether, and is extracted with ether. The combined organic phases are washed with water and with brine, dried and filtered and the solvent is removed in vacuo to give N-ethoxy-1-methyl-3-[4-(1-methylpropoxy)phenyl]propylamine, MS m/e 265 (M ).

nmr (CDCl$_3$) δ 0.80–1.35 (d and t overlapped, 12 H, CH$_3$-CH$_2$-CH(CH$_3$)-O, CH(CH$_3$)-NH, O-CH$_2$-CH$_3$), 1.35–2.03 (m, 4 H, CH$_3$-CH$_2$-CH(CH$_3$)-O, CH$_2$-CH$_2$-CH(CH$_3$)-NH), 2.59 (t, J=8.35, 2 H, CH$_2$-CH$_2$-CH(CH$_3$)-NH), 2.80–3.25 (m, 1 H, CH(CH$_3$)-NH), 3.71 (q, J=6.82, 2 H, O-CH$_2$-CH$_3$), 4.08–4.23 (m, 1 H, CH(CH$_3$)-O), 5.16 (s, NH) and 6.75–7.15 ppm (m, 4 H, aromatic).

What is claimed is:

1. A compound selected from the following formulas:

$$R-(W^1)_m-\underset{Z}{\underset{|}{\bigcirc}}-(W)_{m'}-\underset{R^2}{\underset{|}{(C)_n}}-\underset{R^4}{\underset{|}{(C)_{n'}}}-\underset{}{\overset{R^5}{\underset{|}{C}}}=N-O-R^7 \quad (A)$$

$$R-(W^1)_m-\underset{Z}{\underset{|}{\bigcirc}}-(W)_{m'}-\underset{R^2}{\underset{|}{(C)_n}}-\underset{R^4}{\underset{|}{(C)_{n'}}}-\underset{R^6}{\underset{|}{\overset{R^5}{\underset{|}{C}}}}-O-N=C-R^8 \quad (B)$$

$$R-(W^1)_m-\underset{Z}{\underset{|}{\bigcirc}}-(W)_{m'}-\underset{R^2}{\underset{|}{(C)_n}}-\underset{R^4}{\underset{|}{(C)_{n'}}}-\overset{R^5}{\underset{|}{CH}}-NH-O-R^7 \quad (C)$$

$$R-(W^1)_m-\underset{Z}{\underset{|}{\bigcirc}}-(W)_{m'}-\underset{R^2}{\underset{|}{(C)_n}}-\underset{R^4}{\underset{|}{(C)_{n'}}}-\underset{R^6}{\underset{|}{\overset{R^5}{\underset{|}{C}}}}-O-NH-CH-R^8 \quad (D)$$

wherein,
m is zero or one;
m' is one;
each of n and n' is independently zero, one, two or three;
R is lower alkyl, lower alkenyl, lower alkynyl, lower haloalkyl, lower haloalkenyl, lower haloalkynyl, lower alkoxyalkyl, lower alkylthioalkyl, cycloalkyl, halocycloalkyl, or cycloalkylalkyl;
each of R$^1$, R$^2$, R$^3$, R$^4$, R$^5$, R$^6$ and R$^9$ is independently hydrogen or lower alkyl; provided that: (1) when n is one and n' is zero, then R$^1$ and R$^5$ can together form an alkylene bridge of two to four carbon atoms, or (2) when each of n and n' is one, then either R$^1$ and R$^3$ or R$^3$ and R$^5$ or R$^1$ and R$^5$ can together form an alkylene bridge of two to four carbon atoms;
R$^7$ is lower alkyl, lower haloalkyl, lower alkenyl, lower alkynyl, lower alkoxy, lower alkylthio, lower alkoxyalkyl, lower alkylthioalkyl, pyridyl, furyl or thienyl;
R$^8$ is hydrogen or independently chosen from the values of R$^7$;
W is oxygen, sulfur, or carbonyl;

W$^1$ is oxygen, sulfur, sulfinyl, sulfonyl, NR$^9$ or carbonyl; and
Z is hydrogen, lower alkyl, lower haloalkyl or halogen.

2. A compound of the following formula, according to claim 1:

$$R-W^1-\underset{}{\bigcirc}-O-\underset{R^2}{\underset{|}{(C)_n}}-\overset{R^5}{\underset{|}{C}}=N-O-R^7$$

wherein, n is one or two, and W$^1$ is oxygen or sulfur.

3. A compound according to claim 2 wherein R is lower alkyl, lower alkenyl or lower alkoxyalkyl; R$^1$ is hydrogen; and each of R$^2$ and R$^5$ is independently hydrogen or methyl.

4. A compound according to claim 3 wherein R$^7$ is lower alkyl.

5. A compound according to claim 4 wherein R is 1-methylpropyl and W$^1$ is oxygen.

6. The compound 4-(1-methylpropoxy)phenoxyacetone O-ethyloxime, according to claim 5.

7. The compound 4-(1-methylpropoxy)phenoxyacetaldehyde O-ethyloxime, according to claim 5.

8. The compound 2-[4-(1-methylpropoxy)phenoxy]-propionaldehyde Q-ethyloxime, according to claim 5.

9. A compound according to claim 4 wherein R is 1-methylpropyl and W$^1$ is sulfur.

10. A compound according to claim 4 wherein R is 3-methyl-2-butenyl and W$^1$ is oxygen.

11. A compound of the following formula, according to claim 1:

$$R-W^1-\underset{}{\bigcirc}-O-\underset{R^2}{\underset{|}{(C)_n}}-\underset{R^6}{\underset{|}{\overset{R^5}{\underset{|}{C}}}}-O-N=C-R^8$$

wherein, n is one or two and W$^1$ is oxygen or sulfur.

12. A compound according to claim 11 wherein R is lower alkyl, lower alkenyl or lower alkoxyalkyl; each of R$^1$ and R$^5$ is hydrogen; and each of R$^2$ and R$^6$ is independently hydrogen or methyl.

13. A compound according to claim 12 wherein R$^7$ is lower alkyl and R$^8$ is hydrogen or lower alkyl.

14. A compound according to claim 13 wherein n is two, R$^7$ is methyl or ethyl and R$^8$ is hydrogen, methyl or ethyl.

15. The compound propionaldehyde Q-{1-methyl-3-[4-(1-methylpropoxy)phenoxy]propyl}oxime, according to claim 14.

16. The compound acetone O-{1-methyl-3-[4-(1-methylpropoxy)phenoxyl]propyl}oxime, according to claim 14.

17. A compound according to claim 13 wherein n is one, R$^7$ is methyl or ethyl and R$^8$ is hydrogen, methyl or ethyl.

18. A compound according to claim 17 wherein R is 1methylpropyl or 3-methyl-2-butenyl.

19. The compound acetone O-{1-methyl-2-[4-(1-methylpropoxy)phenoxy]ethyl}oxime, according to claim 18.

20. The compound propionaldehyde O-{1-methyl-2-[4-(1-methylpropoxy)phenoxy]ethyl}oxime, according to claim 16.

21. The compound propionaldehyde O-{2-[4-(1-methylpropoxy)phenoxy]ethyl}oxime, according to claim 18.

22. The compound propionaldehyde O-{2-[4-(1-methylpropoxy)proply}oxime, according to claim 18.

* * * * *